United States Patent
Namkoong et al.

(10) Patent No.: US 8,185,324 B2
(45) Date of Patent: May 22, 2012

(54) METHOD OF DETERMINING INITIAL CONCENTRATION OF NUCLEIC ACID IN SAMPLE USING REAL-TIME AMPLIFICATION DATA

(75) Inventors: Kak Namkoong, Seoul (KR); Young-sun Lee, Yongin-si (KR); Chin-sung Park, Yongin-si (KR); Joo-won Rhee, Daejeon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 672 days.

(21) Appl. No.: 12/259,548

(22) Filed: Oct. 28, 2008

(65) Prior Publication Data

US 2009/0150085 A1    Jun. 11, 2009

(30) Foreign Application Priority Data

Dec. 6, 2007 (KR) .......................... 10-2007-0126378

(51) Int. Cl.
*G01N 33/48* (2006.01)

(52) U.S. Cl. ....................................................... 702/20

(58) Field of Classification Search .................... 702/20
See application file for complete search history.

(56) References Cited

U.S. PATENT DOCUMENTS

| 6,387,621 | B1 | 5/2002 | Wittwer | |
|---|---|---|---|---|
| 2002/0058262 | A1* | 5/2002 | Sagner et al. | 435/6 |
| 2006/0009916 | A1 | 1/2006 | Li et al. | |
| 2006/0088833 | A1 | 4/2006 | Bange et al. | |
| 2006/0129331 | A1 | 6/2006 | Akilesh et al. | |
| 2006/0204972 | A1 | 9/2006 | Kurnik | |
| 2006/0224330 | A1 | 10/2006 | Kurnik | |
| 2007/0073489 | A1 | 3/2007 | Kurnik | |
| 2007/0073490 | A1 | 3/2007 | Kurnik | |
| 2007/0143385 | A1 | 6/2007 | Kurnik et al. | |
| 2008/0299583 | A1* | 12/2008 | Shain et al. | 435/6 |

FOREIGN PATENT DOCUMENTS

| JP | 2002-238585 A | 8/2002 |
|---|---|---|
| JP | 2003-185659 A | 7/2003 |

OTHER PUBLICATIONS

Rossen M. Donev et al., "A quantitative method for comparison of expression of alternatively spliced genes using different primer pairs," Journal of Biochemical and Biophsyical Methods, Nov. 10, 2005, pp. 23-31, No. 66.

* cited by examiner

*Primary Examiner* — Jerry Lin
(74) *Attorney, Agent, or Firm* — Sughrue Mion, PLLC (57) ABSTRACT

Disclosed is a method of determining an initial concentration of a target nucleic acid within a sample using real-time nucleic acid amplification data. Amplification efficiencies of the target nucleic acid with respect to amplification time are obtained from signals of amplified products, and an amplification efficiency function with respect to amplification time is formulated employing the amplification efficiencies.

25 Claims, 4 Drawing Sheets

METHOD OF DETERMINING INITIAL CONCENTRATION OF NUCLEIC ACID IN SAMPLE USING REAL-TIME AMPLIFICATION DATA

CROSS-REFERENCE TO RELATED PATENT APPLICATION

This application claims the benefit of Korean Patent Application No. 10-2007-0126378, filed on Dec. 6, 2007, in the Korean Intellectual Property Office, the disclosure of which is incorporated herein in its entirety by reference.

BACKGROUND OF THE INVENTION

1. Field of the Invention

The present invention relates to a method of determining an initial concentration of a target nucleic acid in a sample using real-time amplification data.

2. Description of the Related Art

Among many analytical methods of detecting and quantifying nucleic acids, PCR is one of the most commonly used methods, the principles of which are disclosed in U.S. Pat. Nos. 4,683,195 and 4,683,202.

Conventional PCR generally shows qualitative, end point results of an amplified DNA using electrophoresis, having drawbacks with regards to accurate quantitative detection of DNA. In order to overcome such drawbacks, a real-time PCR which makes DNA quantification possible using an optical signal agent such as a fluorescent dye and an optical detection system by detecting the optical (e.g., fluorescent) signal intensity directly proportional to the amplified DNA concentration has been developed.

A conventional method of quantifying an initial concentration of a nucleic acid using a nucleic acid amplification data is disclosed in U.S. Pat. Nos. 6,303,305 and 6,503,720. Here, a method of obtaining an initial concentration of a nucleic acid by amplifying a nucleic acid and obtaining a function representing the amount of amplified nucleic acid in each cycle of the amplification, and finding the nth derivative of the function is disclosed. U.S. Pat. No. 6,303,305 discloses a quantification method which takes the maximum value of the derivative as $C_t$ (threshold cycle), and U.S. Pat. No. 6,503,720 discloses a quantification method which takes zero value of the derivative as $C_t$.

In addition, another conventional method of quantifying initial concentration of a nucleic acid using nucleic acid amplification data is disclosed in U.S. Patent Laid-open Publication No. 20020031768. Here, a method of quantifying nucleic acid concentration using a specific value of a derivative is provided.

In addition, in U.S. Patent Publication No. 20060047443, a method of determining an initial concentration of a nucleic acid using real-time nucleic acid amplification data based on a mathematical model of a correlation between the amount of nucleic acid amplified and the amplification cycle is disclosed, which, without using a derivative, calculates the initial concentration using the amplification cycle number or the amplification time corresponding to half the value of the intensity of maximum fluorescent signal subtracted by the background optical (e.g., fluorescent) signal, the amplification cycle or the amplification time corresponding to a maximum amplification efficiency, and the optical signal (e.g., fluorescence) intensity of a prior-to-amplification optical (e.g., fluorescent) signal of the nucleic acid subtracted by the background signal. The content disclosed in U.S. Patent Publication No. 20060047443 is included in the present invention in its entirety by reference.

However, there is still needs for a method of efficiently determining an initial concentration of nucleic acid in a sample.

SUMMARY OF THE INVENTION

The present invention provides an efficient method of determining an initial concentration of a target nucleic acid in a sample. The method may use an amplification efficiency function.

According to an aspect of the present invention, there is provided a method of determining an initial concentration of a target nucleic acid in a sample using real-time nucleic acid amplification data, the method including: amplifying a target nucleic acid and measuring signals from the amplified product; obtaining amplification efficiencies of the target nucleic acid with respect to time using the signals, thereby formulating an amplification efficiency function with respect to the amplification time, wherein the amplification efficiency function is composed of geometric mean values of the amplification efficiency with respect to time; calculating a time at which the amplification efficiency has a maximum value from the amplification efficiency function; and determining the initial concentration of the target nucleic acid within the sample using the calculated amplification time, wherein the initial concentration is determined previously or simultaneously performing the above processes with the target nucleic acid of known varying initial concentrations.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described more fully with reference to the accompanying drawings, in which exemplary embodiments of the invention are shown.

The present invention provides a method of determining an initial concentration of a target nucleic acid within a sample using real-time nucleic acid amplification data.

According to an embodiment of the present invention, the method includes amplifying a target nucleic acid and measuring signals from an amplified product the signals each being measured at different points of time during the amplification; obtaining amplification efficiencies of the target nucleic acid with respect to amplification time using the signals, thereby formulating an amplification efficiency function with respect to amplification time, wherein the amplification efficiency function is composed of geometric mean values of the amplification efficiency with respect to amplification time; calculating a point of the amplification time at which the amplification efficiency has a maximum value by applying the amplification efficiency function; and determining the initial concentration of the target nucleic acid within a sample using the calculated point of the amplification time. The initial concentration is determined using a reference curve obtained by performing the above processes with the target nucleic acid of various known initial concentrations. The reference curve may be obtained by performing previously or simultaneously the above processes with the target nucleic acid of various known initial concentrations.

The present invention includes amplifying a target nucleic acid and measuring signals from the product of the amplification. The amplification method may be a known nucleic acid amplifying method requiring a thermal cycle, such as polymerase chain reaction (PCR), (reverse-transcriptase polymerase chain reaction) RT-PCR, nested PCR, or ligase chain reaction (LCR), but isothermal nucleic acid amplification methods such as strand displacement amplification (SDA), nucleic acid sequence based amplification (NASBA), transcription-mediated amplification (TMA), and rolling circle amplification (RCA) may also be used. In an embodiment, PCR may be used. Nucleic acids include not only DNA and RNA, but also the analogues thereof, such as peptide nucleic acid (PNA). The methods of amplification above are well known to those skilled in the art.

The signals may be selected from fluorescent signals, electrical signals and radioactive signals, but are not limited thereto. The fluorescent signals, for example, may include a hybridization probe with a fluorescent tag, such as a fluorescent resonance energy transfer (FRET) hybridization probe, a molecular beacon, or a probe tagged by two components, where one component is excited by light, and the other component quenches the light emitted. The signals may include a DNA binding dye or an intercalating dye. The DNA binding dye emits a fluorescent signal by reacting with a double-stranded nucleic acid after being excited by light. An electrical signal can be measured, for example, using a method disclosed in U.S. Pat. No. 7,135,294.

Moreover, the present invention includes obtaining amplification efficiencies of the target nucleic acid with respect to amplification time using the signal, thereby formulating an amplification efficiency function with respect to amplification time, wherein the function is composed of geometric mean values of the amplification efficiency with respect to amplification time.

The amplification time refers to a time elapsed from the initiation of the amplification, and may also be represented as a cycle number. Therefore, in the present specification and the claims, time is substitutable with the cycle number.

The amplification efficiency may be represented by Formula 1 below:

$$E_n = \frac{R_n - R_{n-1}}{R_{n-1}} \quad \text{(Formula 1)}$$

wherein $E_n$ refers to an amplification efficiency at $n^{th}$ cycle, $R_{n-1}$ refers to an amplification signal at $(n-1)^{th}$ amplification cycle, and $R_n$ refers to an amplification signal at $n^{th}$ amplification cycle, and n refers to an integer greater than 2.

The amplification efficiency may also be represented by Formula 2 below:

$$E_n = \frac{R_n - R_{n-1}}{R_{n-1} + R_b} \quad \text{(Formula 2)}$$

wherein $E_n$ refers to an amplification efficiency at $n^{th}$ cycle, $R_{n-1}$ refers to an amplification signal at $(n-1)^{th}$ amplification cycle, and $R_n$ refers to an amplification signal at $n^{th}$ amplification cycle, $R_b$ is a non-zero constant, and n refers to an integer greater than 2.

Referring to Formula 2, $R_b$ may be selected from the group consisting of an initial signal value, an amplification signal value at a first amplification cycle, and a value which makes the maximum amplification efficiency represented by Formula 2 1.0.

Referring to Formula 2, in the case where $R_b$ is 0 and the minimum value of the signal intensity according to the amplification $R_{min}$ is around 0, the graph may have a very sharp curve. Moreover, when $R_b$ is 0, the cycle number at which the maximum amplification efficiency occurs may be reproducible, but the cycle number may be too small and the reliability of the maximum amplification efficiency value may decrease, compared to when $R_b$ is not 0.

In contrast, in the case where $R_b$ is not 0, the accuracy of the cycle number at which maximum amplification efficiency occurs, and the reliability of the maximum amplification efficiency value may increase.

Hereinafter, constants that can be used as a value for $R_b$ will be examined, and the improvements at each case will be examined. In the following embodiments, a fluorescent signal is employed as a signal.

First, a background fluorescent signal intensity $(R_b)_{sigmoidal}$, calculated through a sigmoidal model (Formula 13 below) obtained by curve fitting experimental data of a correlation between the fluorescent signal intensity with respect to the amplification cycle number, may be used as $R_b$.

Second, in the case where the fluorescent signal intensity along the amplification cycle starts with a non-zero value, decreases due to photo-bleaching and increase back due to nucleic acid amplification, the initial fluorescent signal intensity (i.e. at amplification cycle=0) can be empirically determined, which can be used as $R_b$. For example, if the initial fluorescent signal intensity is 0.01 on average, 0.01 can be used as the $R_b$ value. This method, insofar as reagents, a fluorescent dye, and the exposure time of the fluorescent dye to light remain unchanged, may be advantageous in that the $R_b$ can be fixed at a constant value after an initial measurement by experiment, since the initial fluorescent signal intensity will be consistent. However, if any one of the reagents, a fluorescent dye, and the exposure time of the fluorescent dye to light changes, the initial fluorescent signal intensity is to be measured in the first experiment to obtain the $R_b$ value.

Third, the nucleic acid fluorescent signal intensity from the first cycle ($R_1$) can be used as $R_b$. This method automatically calibrates the initial fluorescent signal intensity for every experiment even if any one of the reagents, a fluorescent dye, and the exposure time of the fluorescent dye to light changes, and thus may have advantages over the second method, but error becomes larger if the initial fluorescent signal intensity is close to 0.

Fourth, the value which makes the maximum amplification efficiency, which is represented by Formula 2 1.0, may be used as the $R_b$ value. In this method, the $R_b$ value is calculated at cycles where the maximum amplification efficiency occurs, and while this method is the most reasonable method in principle, repetitive calculations are required.

As described in the methods above, the background fluorescent signal intensity $R_b$ may be mainly set using, a background fluorescent signal intensity obtained by a sigmoidal model of Formula 13 (($R_b$)$_{sigmoidal}$), a value corresponding to the initial fluorescent signal intensity (0.01, for example), a fluorescent signal intensity at the first cycle ($R_1$), or a value which makes the maximum amplification efficiency 1.0.

In the case where ($R_b$)$_{sigmoidal}$ is used, curve fitting is required to obtain the value, but for the other values (initial fluorescent signal intensity, $R_1$ etc.), curve fitting is not required.

Besides the four constants for the $R_b$ value described above, in the case where a greater positive real number or a negative real number is used, a similar pattern of the amplification efficiency graph is obtained. Since each graph has a consistent pattern according to the $R_b$ value, any value of $R_b$ except 0 may be used in quantifying the initial concentration of the present invention.

In the case where $R_b$ value is 0, the minimum value for the fluorescent signal intensity becomes close to 0, (that is, $R_b = R_{min} = 0$) and the denominator ($R_{n-1}$) in Formula 13 becomes close to 0, which causes the amplification efficiency ($E_n$) to become unrealistically large, $E_{max}$ peak to be very sharp, and the signals to be greatly affected by noise. In the case where $R_b$ value is not 0, the amplification efficiency exhibits a consistent pattern. However, when $R_1$ is used as $R_b$, an amplification efficiency of greater than 1 appears in the earlier cycles (cycle number≦5) of the amplification with a very sharp peak. Since in a general nucleic acid amplification method, however, the initial rapid amplification of nucleic acids does not occur and an amplification efficiency of greater than 1 does not hold any physical meaning, such a peak might be ignored.

Next, the correlation between the initial concentration of a nucleic acid and % CV (=Standard Deviation/Average) of an amplification cycle number having the maximum amplification efficiency is observed. When the $R_b$ value is above a predetermined level, the % CV value does not vary much. Therefore, when the % CV is to be enhanced while maintaining the amplification efficiency within the range of 0 and 1, $R_1$, the initial fluorescent signal intensity, and ($R_b$)$_{sigmoidal}$ may be used preferably as the $R_b$ value.

Even a small amount of increase in the % CV value of the amplification cycle number having maximum amplification efficiency may cause a large error in quantifying the initial concentration of a nucleic acid, and therefore an accurate quantification method is required.

When formulating the amplification efficiency function, the geometrical mean value may be represented by any one of Formulae 3 and 4 below. Each of Formulae 3 and 4, calculates a geometric mean value of amplification efficiencies of the $n^{th}$ cycle and the cycles just before and after the $n^{th}$ cycle. Formulae 3 and 4 represent a geometric mean value of 3 and 5 consecutive amplification efficiencies, respectively.

$$\overline{E}_{n,c3} = [(1+E_{n-1})(1+E_n)(1+E_{n+1})]^{1/3} - 1 \quad \text{(Formula 3)}$$

wherein $\overline{E}_{n,c3}$ is a geometric mean value of 3 consecutive amplified efficiencies $E_{n-1}$, $E_n$, and $E_{n+1}$, and $E_{n-1}$, $E_n$, and $E_{n-1}$ are amplification efficiencies at $(n-1)^{th}$, $n^{th}$, and $(n+1)^{th}$ cycles respectively, in which n is an integer greater than or equal to 3; in which n is an integer greater than or equal to 4, $$\overline{E}_{n,c5} = [(1+E_{n-2})(1+E_{n-1})(1+E_n)(1+E_{n+1})(1+E_{n+2})]^{1/5} - 1 \quad \text{(Formula 4)}$$

wherein $\overline{E}_{n,c5}$ is a geometric mean value of 5 consecutive amplified efficiencies $E_{n-2}$, $E_{n-1}$, $E_n$, $E_{n+1}$, and $E_{n+2}$, and $E_{n-2}$, $E_{n-1}$, $E_{n+1}$, and $E_{n+2}$ are amplification efficiencies at $(n-2)^{th}$, $(n+1)^{th}$, $n^{th}$, $(n+1)^{th}$, and $(n+2)^{th}$ cycles respectively, in which n is an integer greater than or equal to 4.

When formulating the amplification efficiency function, the geometrical mean value may also be represented by any one of Formulae 5 to 8 below. Formulae 5 to 8, each of which includes an $n^{th}$ cycle, are geometric mean values for amplification efficiencies before the $n^{th}$ cycle. Formulae 5 to 8 represent 2 to 5 geometric mean values of consecutive amplification efficiencies, respectively.

$$\overline{E}_{n,b2} = [(1+E_{n-1})(1+E_n)]^{1/2} - 1 \quad \text{(Formula 5)}$$

wherein $\overline{E}_{n,b2}$ is a geometric mean value of $E_n$ and $E_{n-1}$, and $E_n$, and $E_{n-1}$ are amplification efficiencies at $n^{th}$, and $(n-1)^{th}$ cycles respectively, in which n is an integer greater than or equal to 3, $$\overline{E}_{n,b3} = [(1+E_{n-2})(1+E_{n-1})(1+E_n)]^{1/3} - 1 \quad \text{(Formula 6)},$$

wherein $\overline{E}_{n,b3}$ is a geometric mean value of $E_{n-2}$, $E_{n-1}$ and $E_n$, and $E_{n-2}$, $E_{n-1}$ and $E_n$ are amplification efficiencies at $(n-2)^{th}$, $(n-1)^{th}$, and $n^{th}$ cycles respectively, in which n is an integer greater than or equal to 4, $$\overline{E}_{n,b4} = [(1+E_{n-3})(1+E_{n-2})(1+E_{n-1})(1+E_n)]^{1/4} - 1 \quad \text{(Formula 7)}$$

wherein $\overline{E}_{n,b4}$ is a geometric mean value of $E_{n-3}$, $E_{n-2}$, $E_{n-1}$ and $E_n$, and $E_{n-3}$, $E_{n-2}$, $E_{n-1}$ and $E_n$ are amplification efficiencies at $(n-3)^{th}$, $(n-2)^{th}$, $(n-1)^{th}$, and $n^{th}$ cycles respectively, in which n is an integer greater than or equal to 5, and $$\overline{E}_{n,b5} = [(1+E_{n-4})(1+E_{n-3})(1+E_{n-2})(1+E_{n-1})(1+E_n)]^{1/5} - 1 \quad \text{(Formula 8)},$$

wherein $\overline{E}_{n,b5}$ is a geometric mean value of $E_{n-4}$, $E_{n-3}$, $E_{n-2}$, $E_{n-1}$ and $E_n$, and $E_{n-4}$, $E_{n-3}$, $E_{n-2}$, $E_{n-1}$ and $E_n$ are amplification efficiencies at $(n-4)^{th}$, $(n-3)^{th}$, $(n-2)^{th}$, $(n-1)^{th}$, and $n^{th}$ cycles respectively, in which n is an integer greater than or equal to 6.

When formulating the amplification efficiency function, the geometrical mean value may also be represented by any one of Formulae 9 to 12 below. Formulae 9 to 12, each of which includes an nth cycle, are geometric mean values for consecutive amplification efficiencies after the nth cycle. Formulae 9 to 12 represent 2 to 5 geometric mean values of consecutive amplification efficiencies, respectively.

$$\overline{E}_{n,f2} = [(1+E_n)(1+E_{n+1})]^{1/2} - 1 \quad \text{(Formula 9)},$$

wherein $\overline{E}_{n,f2}$ is a geometric mean value of $E_n$ and $E_{n+1}$, and $E_n$ and $E_{n+1}$ are amplification efficiencies at $n^{th}$ and $(n+1)^{th}$ cycle respectively, in which n is an integer greater than or equal to 2, $$\overline{E}_{n,f3} = [(1+E_n)(1+E_{n+1})(1+E_{n+2})]^{1/3} - 1 \quad \text{(Formula 10)}$$

wherein $\overline{E}_{n,f3}$ is a geometric mean value of $E_n$, $E_{n+1}$, and $E_{n+2}$, and $E_n$, $E_{n+1}$ and $E_{n+2}$ are amplification efficiencies at $n^{th}$, $(n+1)^{th}$, and $(n+2)^{th}$ cycle respectively, in which n is an integer greater than or equal to 2, $$\overline{E}_{n,f4} = [(1+E_n)(1+E_{n+1})(1+E_{n+2})(1+E_{n+3})]^{1/4} - 1 \quad \text{(Formula 11)},$$

wherein $\overline{E}_{n,f4}$ is a geometric mean value of $E_n$, $E_{n+1}$, $E_{n+2}$ and $E_{n+3}$, and $E_n$, $E_{n+1}$, $E_{n+2}$ and $E_{n+3}$ are amplification efficiencies at $n^{th}$, $(n+1)^{th}$, $(n+2)^{th}$, and $(n+3)^{th}$ cycle respectively, in which n is an integer greater than or equal to 2, $$\overline{E}_{n,f5} = [(1+E_n)(1+E_{n+1})(1+E_{n+2})(1+E_{n+3})(1+E_{n+4})]^{1/5} - 1 \quad \text{(Formula 12)},$$

wherein $\overline{E}_{n,f5}$ is a geometric mean value of $E_n$, $E_{n+1}$, $E_{n+2}$, $E_{n+3}$ and $E_{n+4}$ and $E_n$, $E_{n+1}$, $E_{n+2}$, $E_{n+3}$ and $E_{n+4}$ are amplification efficiencies at $n^{th}$, $(n+1)^{th}$, $(n+2)^{th}$, $(n+3)^{th}$, and $(n+4)^{th}$ cycles respectively, in which n is an integer greater than or equal to 2.

When formulating the amplification efficiency function, the function may be obtained by curve fitting. Curve fitting may be performed using at least one of $n^{th}$ degree polynomial equation, in which n is an integer greater than or equal to 2, a sine or a cosine function, a Gaussian distribution function, and a cubic spline interpolation method. Curve fitting is well understood by those of ordinary skill in the art, and an appropriate curve fitting method may be selected to produce a function for geometrical mean efficiencies with respect to time.

The amplification efficiency and curve fitting are described in, for example, a co-pending application U.S. Application Publication No. 2006-0047443 A, contents of which is incorporated herein by reference.

k) in the function obtained by a mathematical model such as Formula 13, non-linear equations of Formulae 15 and 16a to 16d below can be obtained, which may be solved using the Newton-Raphson method:

$$\frac{\partial \varepsilon^2}{\partial R_b} = 0, \; \frac{\partial \varepsilon^2}{\partial R_{max}} = 0, \; \frac{\partial \varepsilon^2}{\partial n_{1/2}} = 0, \; \frac{\partial \varepsilon^2}{\partial k} = 0 \qquad \text{(Formula 15)}$$

wherein, $\varepsilon^2$ is as defined in Formula 14.

$$\sum_n \left[ R_n - \left( R_b + \frac{R_{max}}{1 + e^{-\frac{(n-n_{1/2})}{k}}} \right) \right] = 0, \qquad \text{(Formula 16a)}$$

$$\sum_n \left[ \left\{ R_n - \left( R_b + \frac{R_{max}}{1 + e^{-\frac{(n-n_{1/2})}{k}}} \right) \right\} \times \frac{1}{1 + e^{-\frac{(n-n_{1/2})}{k}}} \right] = 0, \qquad \text{(Formula 16b)}$$

$$\sum_n \left[ \left\{ R_n - \left( R_b + \frac{R_{max}}{1 + e^{-\frac{(n-n_{1/2})}{k}}} \right) \right\} \times \frac{e^{-\frac{(n-n_{1/2})}{k}}}{\left\{1 + e^{-\frac{(n-n_{1/2})}{k}}\right\}^2} \right] = 0, \qquad \text{(Formula 16c)}$$

$$\sum_n \left[ \left\{ R_n - \left( R_b + \frac{R_{max}}{1 + e^{-\frac{(n-n_{1/2})}{k}}} \right) \right\} \times \frac{(n-n_{1/2}) e^{-\frac{(n-n_{1/2})}{k}}}{\left\{1 + e^{-\frac{(n-n_{1/2})}{k}}\right\}^2} \right] = 0. \qquad \text{(Formula 16d)}$$

Real-time PCR data may be modelled as a function of a fluorescent signal with respect to time. For example, the data may be modelled as a function using a sigmoidal model. Moreover, the data may be modelled as a mathematical equation of Formula 13 below:

$$R = R_b + \frac{R_{max}}{1 + e^{-\frac{(n-n_{1/2})}{k}}} \qquad \text{(Formula 13)}$$

Referring to Formula 13, R is a fluorescent signal of the amplified target nucleic acid, $R_b$ is a background fluorescent signal, $R_{max}$ is a maximum fluorescent signal intensity of the amplified target nucleic acid, n is an amplification cycle number, $n_{1/2}$ is an amplification cycle number corresponding to half the value of a maximum value of the fluorescent signal of the amplified target nucleic acid subtracted by a background signal, and k is a constant representing the slope of an increase in the fluorescent signals.

An error between the mathematical model and actual PCR experiment data can be calculated using Formula 14 below:

$$\varepsilon^2 = \sum_n \left[ R_n - \left\{ R_b + \frac{R_{max}}{1 + e^{-\frac{(n-n_{1/2})}{k}}} \right\} \right]^2 \qquad \text{(Formula 14)}$$

Referring to Formula 14, $R_n$ is a fluorescent signal of the amplified target nucleic acid actually obtained by experiment at $n^{th}$ cycle. $R_b$, $R_{max}$, n, $n_{1/2}$, and k are as previously described.

When a least square fitting is used in order to obtain the values corresponding to each parameter ($R_b$, $R_{max}$, $n_{1/2}$, and Moreover, the fluorescent signal intensity prior to amplification of the target nucleic acid except the background fluorescent signal (Rb) is when n=0 in Formula 13, which is defined as Formula 17 below:

$$R_o = \frac{R_{max}}{1 + e^{\frac{n_{1/2}}{k}}}. \qquad \text{(Formula 17)}$$

The method of the present invention includes calculating a time at which the amplification efficiency has a maximum value in the function. The time at which the amplification efficiency function has a maximum value may be calculated using curve fitting near the point where the maximum value occurs. For example, when data of three points on the curve are known, the time can be calculated, using a parabolic curve fitting in order to obtain an x value corresponding to the maximum value on the y axis.

First, a mathematical equation of Formula 18a below is established with regards to 3 coordinates ($x_1$, $y_1$), ($x_2$, $y_2$), and ($x_3$, $y_3$).

$$y_1 = ax_1^2 + bx_1 + c, y_2 = ax_2^2 + bx_2 + c, y_3 = ax_3^2 + bx_3 + c \qquad \text{(Formula 18a)}$$

This can be rearranged into a matrix, as represented by Formula 18b below:

$$\begin{pmatrix} x_1^2 & x_1 & 1 \\ x_2^2 & x_2 & 1 \\ x_3^2 & x_3 & 1 \end{pmatrix} \begin{pmatrix} a \\ b \\ c \end{pmatrix} = \begin{pmatrix} y_1 \\ y_2 \\ y_3 \end{pmatrix}. \qquad \text{(Formula 18b)}$$

Here, defining that $$\begin{vmatrix} x_1^2 & x_1 & 1 \\ x_2^2 & x_2 & 1 \\ x_3^2 & x_3 & 1 \end{vmatrix} = \det(A),$$

constants a, b, and c may be obtained as Formula 18c below:

$$a = \begin{vmatrix} y_1 & x_1 & 1 \\ y_2 & x_2 & 1 \\ y_3 & x_3 & 1 \end{vmatrix} \Big/ \det(A)$$ (Formula 18c)

$$b = \begin{vmatrix} x_1^2 & y_1 & 1 \\ x_2^2 & y_2 & 1 \\ x_3^2 & y_3 & 1 \end{vmatrix} \Big/ \det(A)$$

$$c = \begin{vmatrix} x_1^2 & x_1 & y_1 \\ x_2^2 & x_2 & y_2 \\ x_3^2 & x_3 & y_3 \end{vmatrix} \Big/ \det(A).$$

Next, $x_{max}$ can be obtained from Formula 18d below:

$$X_{max} = -\frac{b}{2a} = \frac{y_1(x_2^2 - x_3^2) + y_2(x_3^2 - x_1^2) + y_3(x_1^2 - x_2^2)}{2[y_1(x_2 - x_3) + y_2(x_3 - x_1) + y_3(x_1 - x_2)]}.$$ (Formula 18d)

Hitherto, a method of obtaining a fluorescent signal function from amplified target nucleic acid with respect to amplification time using a mathematical model, and a method of obtaining each parameter of the function have been described. The parameters have the following correlation with the initial concentration of the target nucleic acid: as the initial concentration of the target nucleic acid increases, the amplification cycle number corresponding to half the value of the maximum fluorescent signal ($n_{1/2}$) and the cycle number at which the maximum amplification efficiency appears ($n_{Emax}$) decreases. Moreover, the slope of a standard curve obtained using a method of determining the initial concentration of the nucleic acid using conventional derivatives becomes very similar to the slope of the standard curve obtained using the amplification cycle number corresponding to half the value of the maximum fluorescent signal ($n_{1/2}$) and the maximum amplification efficiency ($n_{Emax}$). However, the amplification cycle number corresponding to the maximum amplification efficiency ($n_{Emax}$) is smaller than the amplification cycle number corresponding to half the value of the maximum fluorescent signal ($n_{1/2}$) at the same initial concentration of the target nucleic acid, and therefore the initial concentration of the target nucleic acid can be determined with a lower amplification cycle number when $n_{Emax}$ is used.

The method of the present invention includes determining the initial concentration of the target nucleic acid within a sample using the calculated amplification time, wherein the initial concentration is determined using a reference curve obtained from various known initial concentrations of the target nucleic acid. The reference curve may be obtained by previously or simultaneously performing the above processes with the target nucleic acid of various known initial concentrations.

The present invention may also be implemented as codes readable by a computer in recordable media readable with a computer. The recordable media, which is readable by a computer, include all types of recordable devices in which data readable by a computer system is stored. Examples of recordable media readable by a computer include ROM, RAM, CD-ROM, magnetic tape, floppy disk, optical data storage device, as well as carrier waves (transfer through the internet, for example). In addition, recording media readable by a computer can be distributed in a computer system connected to a network, in which codes readable by a computer in a distributed form may be stored and executed.

According to the method of the present invention, the concentration of a nucleic acid within a sample may be determined with a low coefficient of variation (CV) using a function of geometric mean values of amplification efficiency with respect to time.

The present invention will now be described in more detail with reference to the following examples. However, these examples are for illustrative purposes only and are not intended to limit the scope of the invention.

REFERENCE EXAMPLE 1

Measurement of Cycle Number Corresponding to Maximum Fluorescent Signal Using Arithmetic Mean Values of $2^{nd}$ Derivative Function In the present example, PCR was performed using plasmid DNA of Hepatitis type B (7.4 kb, genotype A subtype adw) as a template at concentrations of 1, 10, $10^2$, $10^3$, $10^4$, $10^5$, $10^6$, $10^7$, and $10^8$ copies/µl, and oligonucleotide pairs of SEQ ID NOS. 1 and 2 as primers. The PCR solution composition was as follows:

DNA template (HBV plasmid DNA; 7.4 kb, genotype A subtype adw), 1×SYBR™ Green I (asymmetrical cyanine dye) PCR buffer, 1 mM forward and reverse primers (SEQ ID NOs: 1 and 2, respectively), 200 µM dNTP (deoxynucleotide triphosphate), 5 mM $MgCl_2$, 5% glycerol, 500 mM formamide, 0.2 ng/µl BSA, 1 unit/µl uracil-N-glycosilase, 1 unit/µl Taq polymerase.

PCR was performed in real-time using SYBR™ Green I fluorescent dye in TMC-1000 system (Samsung Electronics Co. Ltd). The PCR conditions included 120 seconds predenaturation at 92° C., 1 second denaturation at 92° C., and 15 seconds annealing and extension at 62° C., repeated 40 times.

The fluorescent signals were measured at the end of the annealing and extension stage for 5 seconds, and the real-time fluorescent signals obtained as above were plotted into a function of a graph, and the function was differentiated twice to obtain a $2^{nd}$ derivative function according to the guide provided by the manufacturer of the PCR device, and the functions were expressed in a diagram.

Figure 1A:
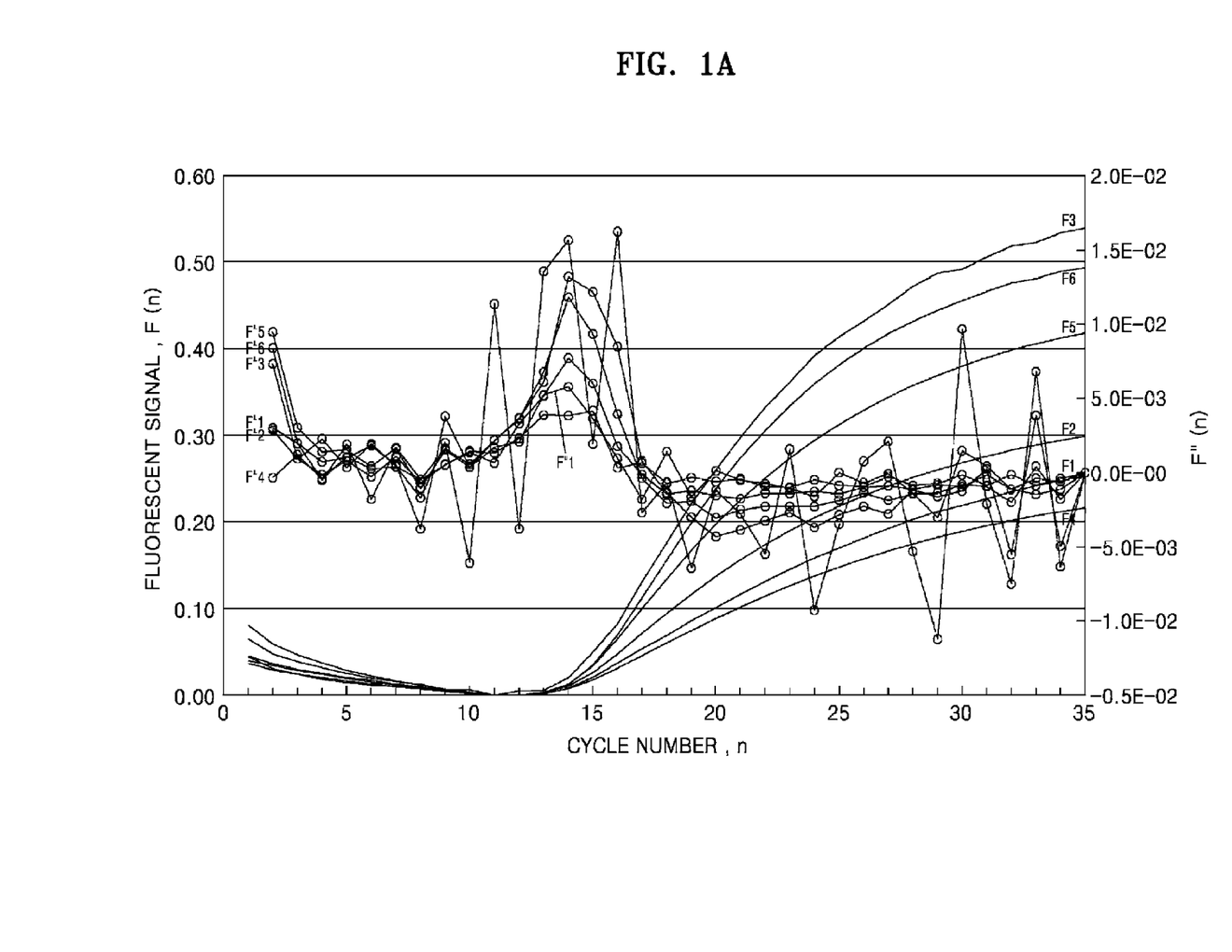
FIG. 1A is a graph illustrating a function corresponding to fluorescent signals measured in real-time and its 2nd derivative function.

FIG. 1A is a graph illustrating a function corresponding to fluorescent signals measured in real-time and its $2^{nd}$ derivative function. Referring to FIG. 1A, the vertical axis on the left represents the fluorescent signal intensity F(n), and the vertical axis on the right represents the $2^{nd}$ derivative value of F(n), that is, F"(n).

Figure 1B:
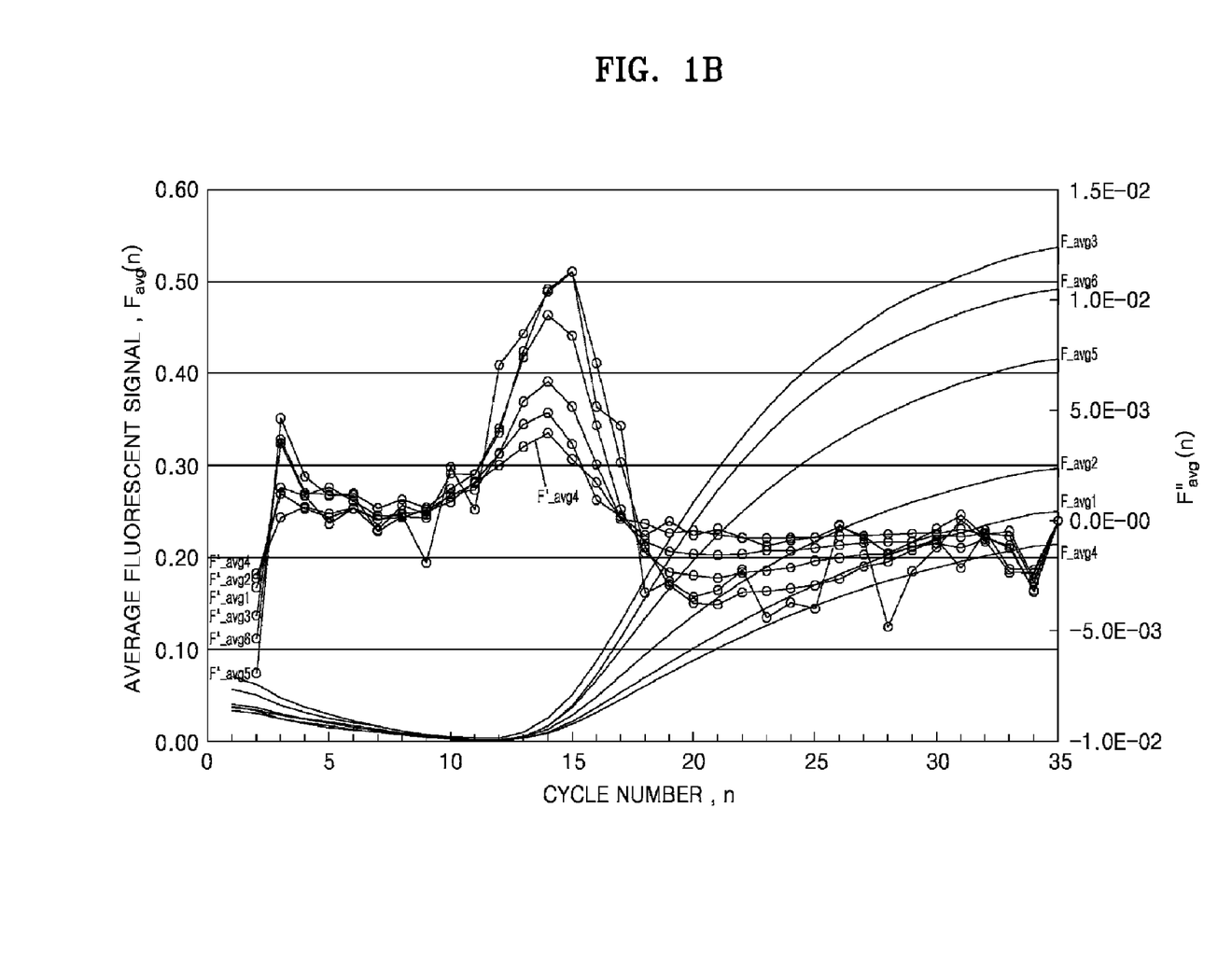
FIG. 1B is a graph illustrating a function of an arithmetic mean of a function corresponding to fluorescent signals measured in real-time obtained from FIG. 1A and a function of an arithmetic mean of its $2^{nd}$ derivative function obtained from FIG. 1A.

FIG. 1B is a graph illustrating a function corresponding to an arithmetic mean of fluorescent signals measured in real-time obtained from FIG. 1A and a function of an arithmetic mean of its $2^{nd}$ derivative function obtained from FIG. 1A. Referring to FIG. 1B, the vertical axis on the left represents the fluorescent signal intensity of arithmetic mean value $F_{avg}(n)$, and the vertical axis on the right represents a $2^{nd}$ derivative value of $F_{avg}(n)$, that is, $F"_{avg}(n)$.

Next, the mean value, standard deviation (SD), and coefficient of variation (% CV) of cycle number corresponding to the maximum value of the $2^{nd}$ derivative function from FIG.

1A were obtained. Furthermore, the mean value, SD, and % CV of a cycle number corresponding to the maximum value of the function of an arithmetic mean of the $2^{nd}$ derivative function from FIG. 1B were obtained. The mean cycle number, SD, and % CV corresponding to the maximum value are shown in Table 1 below:

TABLE 1

| Number | Maximum $2^{nd}$ derivative | Maximum Arithmetic Mean of $2^{nd}$ derivative |
|---|---|---|
| 1 | 13.70 | 13.77 |
| 2 | 14.10 | 13.94 |
| 3 | 15.93 | 14.63 |
| 4 | 14.58 | 13.84 |
| 5 | 14.17 | 14.17 |
| 6 | 14.37 | 14.66 |
| Mean | 14.48 | 14.17 |
| SD | 0.77 | 0.39 |
| % CV | 5.32 | 2.78 |

Referring to Table 1, when a function of the maximum arithmetic mean values of the $2^{nd}$ derivative is used, SD and % CV are reduced. Thus, the accuracy of quantifying the initial concentration of a nucleic acid can be increased.

Example 1

Measurement of Cycle Number Corresponding to Maximum Fluorescent Signal Using Geometric Mean Values of Amplification Efficiency In the present example, the experiment was performed under the same conditions as those of Reference Example 1 to obtain fluorescent signal values in real-time and converted into amplification efficiency represented by Formula 2 below, to obtain an amplification efficiency function:

$$E_n = \frac{R_n - R_{n-1}}{R_{n-1} + R_b} \quad \text{(Formula 2)}$$

wherein $E_n$ refers to an amplification efficiency at $n^{th}$ cycle, $R_{n-1}$ refers to an amplification signal at $(n-1)^{th}$ amplification cycle, and $R_n$ refers to an amplification signal at the $n^{th}$ amplification cycle, and n refers to an integer greater than 2.

Moreover, the amplification efficiency function values were converted to geometric mean values represented by Formula 3 below, to obtain a geometric mean function of the amplification efficiency:

$$\overline{E}_{n,c3} = [(1+E_{n-1})(1+E_n)(1+E_{n+1})]^{1/3} - 1 \quad \text{(Formula 3)}$$

wherein $\overline{E}_{n,c3}$ is a geometric mean value of 3 consecutive amplified efficiencies of $E_{n-1}$, $E_n$, and $E_{n+1}$, and $E_{n-1}$, $E_n$, and $E_{n+1}$ are amplification efficiencies at $(n-1)^{th}$, $n^{th}$, and $(n+1)^{th}$ cycles respectively, in which n is an integer greater than or equal to 3.

Figure 2A:
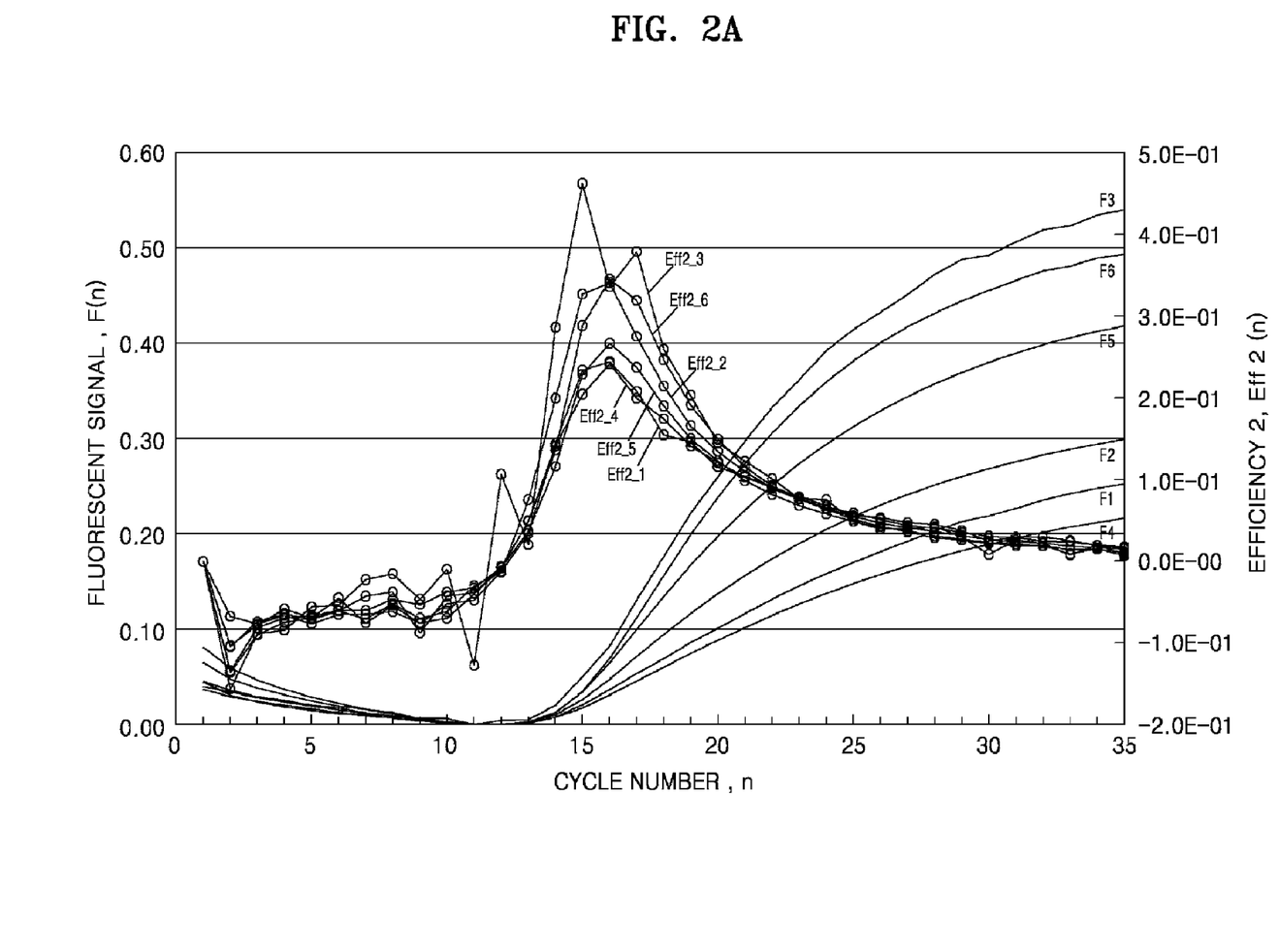
FIG. 2A is a graph illustrating a function corresponding to fluorescent signals measured in real-time and its amplification efficiency function.

FIG. 2A is a graph illustrating a function corresponding to fluorescent signals measured in real-time and its amplification efficiency function.

Figure 2B:
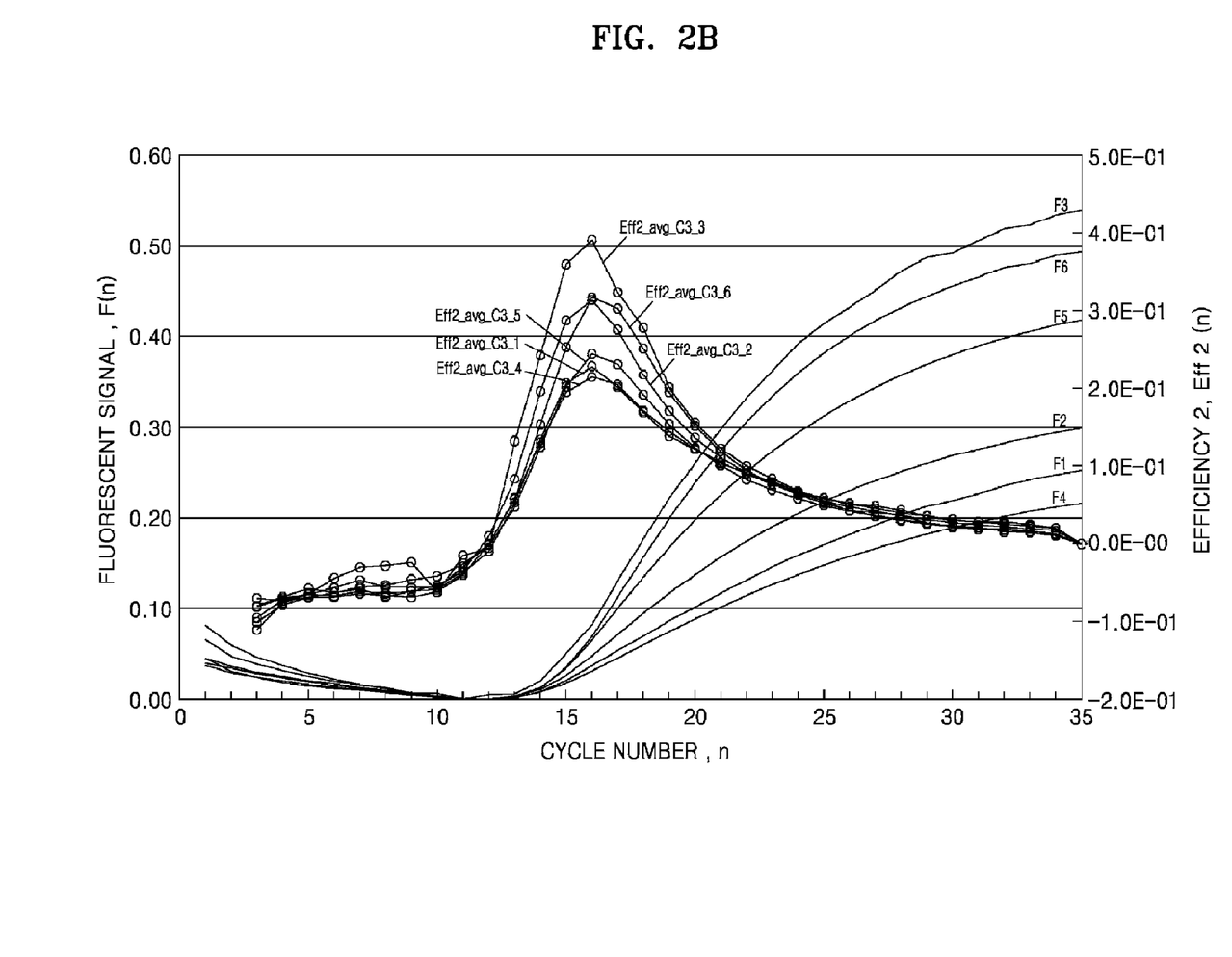
FIG. 2B is a graph illustrating a function corresponding to fluorescent signals measured in real-time obtained from FIG. 2A and a function of a geometric mean value of the amplification efficiency function obtained from FIG. 2A.

FIG. 2B is a graph illustrating a function corresponding to fluorescent signals measured in real-time as in FIG. 2A and a function of a geometric mean of the amplification efficiency obtained from FIG. 2A.

Next, the mean value, SD, and % CV of cycle number corresponding to the maximum value of the amplification efficiency function from FIG. 2A were obtained. Furthermore, the mean value, SD, and % CV of a cycle number corresponding to the maximum value of the geometric mean function of the amplification efficiency function from FIG. 2B were obtained. The mean cycle number, SD, and % CV corresponding to the maximum value are shown in Table 2 below:

TABLE 2

| Number | Maximum Amplification Efficiency | Maximum Geometric Mean of the Amplification Efficiency |
|---|---|---|
| 1 | 15.73 | 15.95 |
| 2 | 15.63 | 15.91 |
| 3 | 15.08 | 15.82 |
| 4 | 15.97 | 16.16 |
| 5 | 16.06 | 16.26 |
| 6 | 16.19 | 16.32 |
| Mean | 15.78 | 16.07 |
| SD | 0.40 | 0.20 |
| % CV | 2.51 | 1.27 |

Referring to Table 2, a Ct value or a characteristic cycle number in the standard curve can be obtained with a low standard deviation and a low coefficient of variation, without using a second derivative or its arithmetic mean function. That is, the quantification accuracy increases when an amplification efficiency function is used, compared to when a second derivative or its arithmetic mean function is used. Moreover, when the geometric mean function of the amplification efficiency was used, the accuracy was the highest.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of determining an initial concentration of a target nucleic acid in a sample using real-time nucleic acid amplification data, the method comprising:
(a) amplifying the target nucleic acid and detecting signals from an amplified product at different points of time during the amplification;
(b) obtaining an amplification efficiency of the target nucleic acid with respect to time using the detected signals, wherein the amplification efficiency is represented by Formula 1 below, $$E_n = \frac{R_n - R_{n-1}}{R_{n-1}} \quad \text{(Formula 1)}$$

wherein $E_n$ refers to an amplification efficiency at $n^{th}$ cycle, $R_{n-1}$ refers to an amplification signal at $(n-1)^{th}$ amplification cycle, and $R_n$ refers to an amplification signal at $n^{th}$ amplification cycle, and n refers to an integer greater than 2;
(c) formulating an amplification efficiency function with respect to amplification time, wherein the amplification efficiency function is composed of geometric mean values of the amplification efficiency with respect to time;
(d) applying the amplification efficiency function to calculate a point of amplification time at which the amplification efficiency has a maximum value; and
(e) determining the initial concentration of the target nucleic acid in the sample using the calculated point of amplification time, wherein the initial concentration is determined using a reference curve, said reference curve being obtained employing the target nucleic acid of various known initial concentrations.

2. The method of claim 1, wherein the signals are one selected from the group consisting of a fluorescent signal, an electrical signal and a radioactive signal.

3. The method of claim 1, wherein the geometric mean value is represented by any one of Formulae 3 and 4 below:

$$\overline{E}_{n,c3} = [(1+E_{n-1})(1+E_n)(1+E_{n+1})]^{1/3} - 1 \quad \text{(Formula 3)}$$

wherein $\overline{E}_{n,c3}$ is a geometric mean value of 3 consecutive amplified efficiencies $E_{n-1}$, $E_n$, and $E_{n+1}$, and $E_{n-1}$, $E_n$, and $E_{n+1}$ are amplification efficiencies at $(n-1)^{th}$, $n^{th}$, and $(n+1)^{th}$ cycles respectively, in which n is an integer greater than or equal to 3;

$$\overline{E}_{n,c5} = [(1+E_{n-2})(1+E_{n-1})(1+E_n)(1+E_{n+1})(1+E_{n+2})]^{1/5} - 1 \quad \text{(Formula 4)},$$

wherein $\overline{E}_{n,c5}$ is a geometric mean value of 5 consecutive amplified efficiencies $E_{n-2}$, $E_{n-1}$, $E_n$, $E_{n+1}$, and $E_{n+2}$, and $E_{n-2}$, $E_{n-1}$, $E_n$, $E_{n+1}$, and $E_{n+2}$ are amplification efficiencies at $(n-2)^{th}$, $(n-1)^{th}$, $n^{th}$, $(n+1)^{th}$, and $(n+2)^{th}$ cycles respectively, in which n is an integer greater than or equal to 4.

4. The method of claim 1, wherein the geometric mean value is represented by any one of Formulae 5 to 8 below:

$$\overline{E}_{n,b2} = [(1+E_{n-1})(1+E_n)]^{1/2} - 1 \quad \text{(Formula 5)},$$

wherein $\overline{E}_{n,b2}$ is a geometric mean value of $E_n$ and $E_{n-1}$, and $E_n$, and $E_{n-1}$ are amplification efficiencies at $n^{th}$, and $(n-1)^{th}$ cycles respectively, in which n is an integer greater than or equal to 3, $$\overline{E}_{n,b3} = [(1+E_{n-2})(1+E_{n-1})(1+E_n)]^{1/3} - 1 \quad \text{(Formula 6)},$$

wherein $\overline{E}_{n,b3}$ is a geometric mean value of $E_{n-2}$, $E_{n-1}$ and $E_n$, and $E_{n-2}$, $E_{n-1}$ and $E_n$ are amplification efficiencies at $(n-2)^{th}$, $(n-1)^{th}$, and $n^{th}$ cycles respectively, in which n is an integer greater than or equal to 4, $$\overline{E}_{n,b4} = [(1+E_{n-3})(1+E_{n-2})(1+E_{n-1})(1+E_n)]^{1/4} - 1 \quad \text{(Formula 7)}$$

wherein $\overline{E}_{n,b4}$ is a geometric mean value of $E_{n-3}$, $E_{n-2}$, $E_{n-1}$ and $E_n$, and $E_{n-3}$, $E_{n-2}$, $E_{n-1}$ and $E_n$ are amplification efficiencies at $(n-3)^{th}$, $(n-2)^{th}$, $(n-1)^{th}$, and $n^{th}$ cycles respectively, in which n is an integer greater than or equal to 5, and $$\overline{E}_{n,b5} = [(1+E_{n-4})(1+E_{n-3})(1+E_{n-2})(1+E_{n-1})(1+E_n)]^{1/5} - 1 \quad \text{(Formula 8)},$$

wherein $\overline{E}_{n,b5}$ is a geometric mean value of $E_{n-4}$, $E_{n-3}$, $E_{n-2}$, $E_{n-1}$ and $E_n$, and $E_{n-4}$, $E_{n-3}$, $E_{n-2}$, $E_{n-1}$ and $E_n$ are amplification efficiencies at $(n-4)^{th}$, $(n-3)^{th}$, $(n-2)^{th}$, $(n-1)^{th}$, and $n^{th}$ cycles respectively, in which n is an integer greater than or equal to 6.

5. The method of claim 1, wherein the geometric mean value is represented by any one of Formulae 9 to 12 below:

$$\overline{E}_{n,f2} = [(1+E_n)(1+E_{n+1})]^{1/2} - 1 \quad \text{(Formula 9)},$$

wherein $\overline{E}_{n,f2}$ is a geometric mean value of $E_n$ and $E_{n+1}$, and $E_n$ and $E_{n+1}$ are amplification efficiencies at $n^{th}$ and $(n+1)^{th}$ cycle respectively, in which n is an integer greater than or equal to 2, $$\overline{E}_{n,f3} = [(1+E_n)(1+E_{n+1})(1+E_{n+2})]^{1/3} - 1 \quad \text{(Formula 10)},$$

wherein $\overline{E}_{n,f3}$ is a geometric mean value of $E_n$, $E_{n+1}$, and $E_{n+2}$, and $E_n$, $E_{n+1}$ and $E_{n+2}$ are amplification efficiencies at $n^{th}$, $(n+1)^{th}$, and $(n+2)^{th}$ cycle respectively, in which n is an integer greater than or equal to 2, $$\overline{E}_{n,f4} = [(1+E_n)(1+E_{n+1})(1+E_{n+2})(1+E_{n+3})]^{1/4} - 1 \quad \text{(Formula 11)},$$

wherein $\overline{E}_{n,f4}$ is a geometric mean value of $E_n$, $E_{n+1}$, $E_{n+2}$ and $E_{n+3}$, and $E_n$, $E_{n+1}$, $E_{n+2}$ and $E_{n+3}$ are amplification efficiencies at $n^{th}$, $(n+1)^{th}$, $(n+2)^{th}$, and $(n+3)^{th}$ cycle respectively, in which n is an integer greater than or equal to 2, $$\overline{E}_{n,f5}=[(1+E_n)(1+E_{n+1})(1+E_{n+2})(1+E_{n+3})(1+E_{n+4})]^{1/5}-1 \quad \text{(Formula 12),}$$

wherein $\overline{E}_{n,f5}$ is a geometric mean value of $E_n$, $E_{n+1}$, $E_{n+2}$, $E_{n+3}$ and $E_{n+4}$, and $E_n$, $E_{n+1}$, $E_{n+2}$, $E_{n+3}$ and $E_{n+4}$ are amplification efficiencies at $n^{th}$, $(n+1)^{th}$, $(n+2)^{th}$, $(n+3)^{th}$, and $(n+4)^{th}$ cycle respectively, in which n is an integer greater than or equal to 2.

6. The method of claim 1, wherein the point of amplification time at which the amplification efficiency has the maximum value according to the amplification efficiency function is calculated using curve fitting near the point of maximum value.

7. The method of claim 6, wherein curve fitting is performed using at least one of an $n^{th}$ degree polynomial equation, in which n is an integer greater than or equal to 2, a sine or a cosine function, a Gaussian distribution function, and a cubic spline interpolation method.

8. The method of claim 1, wherein the reference curve is obtained by performing the steps (a)-(d) on the target nucleic acid of various known initial concentrations.

9. A method of determining an initial concentration of a target nucleic acid in a sample using real-time nucleic acid amplification data, the method comprising:

(a) amplifying the target nucleic acid and detecting signals from an amplified product at different points of time during the amplification;

(b) obtaining an amplification efficiencies efficiency of the target nucleic acid with respect to time using the detected signals, wherein the amplification efficiency is represented by Formula 2 below, $$E_n = \frac{R_n - R_{n-1}}{R_{n-1} + R_b} \quad \text{(Formula 2)}$$

wherein $E_n$ refers to an amplification efficiency at $n^{th}$ cycle, $R_{n-1}$ refers to an amplification signal at $(n-1)^{th}$ amplification cycle, and $R_n$ refers to an amplification signal at $n^{th}$ amplification cycle, $R_b$ is a non-zero constant, and n refers to an integer greater than 2;

(c) formulating an amplification efficiency function with respect to amplification time, wherein the amplification efficiency function is composed of geometric mean values of the amplification efficiency with respect to time;

(d) applying the amplification efficiency function to calculate a point of amplification time at which the amplification efficiency has a maximum value; and (e) determining the initial concentration of the target nucleic acid in the sample using the calculated point of amplification time, wherein the initial concentration is determined using a reference curve, said reference curve being obtained employing the target nucleic acid of various known initial concentrations.

10. The method of claim 9, wherein $R_b$ is selected from the group consisting of an initial signal value, an amplification signal value at the first amplification cycle, and a value at which the maximum amplification efficiency represented by Formula 2 becomes 1.

11. The method of claim 9, wherein the signals are one selected from the group consisting of a fluorescent signal, an electrical signal and a radioactive signal.

12. The method of claim 9, wherein the geometric mean value is represented by any one of Formulae 3 and 4 below:

$$\overline{E}_{n,c3}=[(1+E_{n-1})(1+E_n)(1+E_{n+1})]^{1/3}-1 \quad \text{(Formula 3)}$$

wherein $\overline{E}_{n,c3}$ is a geometric mean value of 3 consecutive amplified efficiencies $E_{n-1}$, $E_n$, and $E_{n+1}$, and $E_{n-1}$, $E_n$, and $E_{n+1}$ are amplification efficiencies at $(n-1)^{th}$, $n^{th}$, and $(n+1)^{th}$ cycles respectively, in which n is an integer greater than or equal to 3;

$$\overline{E}_{n,c5}=[(1+E_{n-2})(1+E_{n-1})(1+E_n)(1+E_{n+1})(1+E_{n+2})]^{1/5}-1 \quad \text{(Formula 4),}$$

wherein $\overline{E}_{n,c5}$ is a geometric mean value of 5 consecutive amplified efficiencies $E_{n-2}$, $E_{n-1}$, $E_n$, $E_{n+1}$, and $E_{n+2}$, and $E_{n-2}$, $E_{n-1}$, $E_n$, $E_{n+1}$, and $E_{n+2}$ are amplification efficiencies at $(n-2)^{th}$, $(n-1)^{th}$, $n^{th}$, $(n+1)^{th}$, $(n+2)^{th}$ cycles respectively, in which n is an integer greater than or equal to 4.

13. The method of claim 9, wherein the geometric mean value is represented by any one of Formulae 5 to 8 below:

$$\overline{E}_{n,b2}=[(1+E_{n-1})(1+E_n)]^{1/2}-1 \quad \text{(Formula 5),}$$

wherein $\overline{E}_{n,b2}$ is a geometric mean value of $E_n$ and $E_{n-1}$, and $E_n$ and $E_{n-1}$ are amplification efficiencies at $n^{th}$, and $(n-1)^{th}$ cycles respectively, in which n is an integer greater than or equal to 3, $$\overline{E}_{n,b3}=[(1+E_{n-2})(1+E_{n-1})(1+E_n)]^{1/3}-1 \quad \text{(Formula 6),}$$

wherein $\overline{E}_{n,b3}$ is a geometric mean value of $E_{n-2}$, $E_{n-1}$ and $E_n$, and $E_{n-2}$, $E_{n-1}$ and $E_n$ are amplification efficiencies at $(n-2)^{th}$, $(n-1)^{th}$, and $n^{th}$ cycles respectively, in which n is an integer greater than or equal to 4, $$\overline{E}_{n,b4}=[(1+E_{n-3})(1+E_{n-2})(1+E_{n-1})(1+E_n)]^{1/4}-1 \quad \text{(Formula 7)}$$

wherein $\overline{E}_{n,b4}$ is a geometric mean value of $E_{n-3}$, $E_{n-2}$, $E_{n-1}$ and $E_n$, and $E_{n-3}$, $E_{n-2}$, $E_{n-1}$ and $E_n$ are amplification efficiencies at $(n-3)^{th}$, $(n-2)^{th}$, $(n-1)^{th}$, and $n^{th}$ cycles respectively, in which n is an integer greater than or equal to 5, and $$\overline{E}_{n,b5}=[(1+E_{n-4})(1+E_{n-3})(1+E_{n-2})(1+E_{n-1})(1+E_n)]^{1/5}-1 \quad \text{(Formula 8),}$$

wherein $\overline{E}_{n,b5}$ is a geometric mean value of $E_{n-4}$, $E_{n-3}$, $E_{n-2}$, $E_{n-1}$ and $E_n$, and $E_{n-4}$, $E_{n-3}$, $E_{n-2}$, $E_{n-1}$ and $E_n$ are amplification efficiencies at $(n-4)^{th}$, $(n-3)^{th}$, $(n-2)^{th}$, $(n-1)^{th}$, and $n^{th}$ cycles respectively, in which n is an integer greater than or equal to 6.

14. The method of claim 9, wherein the geometric mean value is represented by any one of Formulae 9 to 12 below:

$$\overline{E}_{n,f2}=[(1+E_n)(1+E_{n+1})]^{1/2}-1 \quad \text{(Formula 9),}$$

wherein $\overline{E}_{n,f2}$ is a geometric mean value of $E_n$ and $E_{n+1}$, and $E_n$ and $E_{n+1}$ are amplification efficiencies at $n^{th}$ and $(n+1)^{th}$ cycle respectively, in which n is an integer greater than or equal to 2, $$\overline{E}_{n,f3}=[(1+E_n)(1+E_{n+1})(1+E_{n+2})]^{1/3}-1 \quad \text{(Formula 10),}$$

wherein $\overline{E}_{n,f3}$ is a geometric mean value of $E_n$, $E_{n+1}$, and $E_{n+2}$, and $E_n$, $E_{n+1}$ and $E_{n+2}$ are amplification efficiencies at $n^{th}$, $(n+1)^{th}$, and $(n+2)^{th}$ cycle respectively, in which n is an integer greater than or equal to 2, $$\overline{E}_{n,f4}=[(1+E_n)(1+E_{n+1})(1+E_{n+2})(1+E_{n+3})]^{1/4}-1 \quad \text{(Formula 11),}$$

wherein $\overline{E}_{n,f4}$ is a geometric mean value of $E_n$, $E_{n+1}$, $E_{n+2}$ and $E_{n+3}$, and $E_n$, $E_{n+1}$, $E_{n+2}$ and $E_{n+3}$ are amplification efficiencies at $n^{th}$, $(n+1)^{th}$, $(n+2)^{th}$, and $(n+3)^{th}$ cycle respectively, in which n is an integer greater than or equal to 2, $$\overline{E}_{n,f5}=[(1+E_n)(1+E_{n+1})(1+E_{n+2})(1+E_{n+3})(1+E_{n+4})]^{1/5}-1 \quad \text{(Formula 12),}$$

wherein $\overline{E}_{n,f5}$ is a geometric mean value of $E_n$, $E_{n+1}$, $E_{n+2}$, $E_{n+3}$ and $E_{n+4}$, and $E_n$, $E_{n+1}$, $E_{n+2}$, $E_{n+3}$ and $E_{n+4}$ are amplification efficiencies at $n^{th}$, $(n+1)^{th}$, $(n+2)^{th}$, $(n+3)^{th}$, and $(n+4)^{th}$ cycle respectively, in which n is an integer greater than or equal to 2.

15. The method of claim 9, wherein the point of amplification time at which the amplification efficiency has the maximum value according to the amplification efficiency function is calculated using curve fitting near the point of maximum value.

16. The method of claim 15, wherein curve fitting is performed using at least one of an $n^{th}$ degree polynomial equation, in which n is an integer greater than or equal to 2, a sine or a cosine function, a Gaussian distribution function, and a cubic spline interpolation method.

17. The method of claim 9, wherein the reference curve is obtained by performing the steps (a)-(d) on the target nucleic acid of various known initial concentrations.

18. A method of determining an initial concentration of a target nucleic acid in a sample using real-time nucleic acid amplification data, the method comprising:
(a) amplifying a target nucleic acid and detecting signals from an amplified product at different points of time during the amplification;
(b) obtaining an amplification efficiency of the target nucleic acid with respect to time using the detected signals,
(c) formulating an amplification efficiency function comprising geometric mean values of amplification efficiency with respect to time;
(d) applying the amplification efficiency function to calculate a point of amplification time at which the amplification efficiency has a maximum value, wherein the application of the amplification efficiency function increases quantification accuracy relative to the application of an arithmetic mean function; and
(e) determining the initial concentration of the target nucleic acid in the sample using the calculated point of amplification time, wherein the initial concentration is determined using a reference curve, said reference curve being obtained employing the target nucleic acid of various known initial concentrations.

19. The method of claim 18, wherein the point of amplification time at which the amplification efficiency has the maximum value according to the amplification efficiency function is calculated using curve fitting near the point of maximum value.

20. The method of claim 19, wherein curve fitting is performed using at least one of an $n^{th}$ degree polynomial equation, in which n is an integer greater than or equal to 2, a sine or a cosine function, a Gaussian distribution function, and a cubic spline interpolation method.

21. The method of claim 18, wherein the reference curve is obtained by performing the steps (a)-(d) on the target nucleic acid of various known initial concentrations.

22. The method of claim 18, wherein the signals are one selected from the group consisting of a fluorescent signal, an electrical signal and a radioactive signal.

23. The method of claim 18, wherein the geometric mean value is represented by any one of Formulae 3 and 4 below:

$$\overline{E}_{n,c3}=[(1+E_{n-1})(1+E_n)(1+E_{n+1})]^{1/3}-1 \quad \text{(Formula 3)}$$

wherein $\overline{E}_{n,c3}$ is a geometric mean value of 3 consecutive amplified efficiencies $E_{n-1}$, $E_n$, and $E_{n+1}$, and $E_{n-1}$, $E_n$, and $E_{n+1}$ are amplification efficiencies at $(n-1)^{th}$, $n^{th}$, and $(n+1)^{th}$ cycles respectively, in which n is an integer greater than or equal to 3;

$$\overline{E}_{n,c5}=[(1+E_{n-2})(1+E_{n-1})(1+E_n)(1+E_{n+1})(1+E_{n+2})]^{1/5}-1 \quad \text{(Formula 4)},$$

wherein $\overline{E}_{n,c5}$ is a geometric mean value of 5 consecutive amplified efficiencies $E_{n-2}$, $E_{n-1}$, $E_n$, $E_{n+1}$, and $E_{n+2}$, and $E_{n-2}$, $E_{n-1}$, $E_n$, $E_{n+1}$, and $E_{n+2}$ are amplification efficiencies at $(n-2)^{th}$, $(n-1)^{th}$, $n^{th}$, $(n+1)^{th}$, and $(n+2)^{th}$ cycles respectively, in which n is an integer greater than or equal to 4.

24. The method of claim 18, wherein the geometric mean value is represented by any one of Formulae 5 to 8 below:

$$\overline{E}_{n,b2}=[(1+E_{n-1})(1+E_n)]^{1/2}-1 \quad \text{(Formula 5)},$$

wherein $\overline{E}_{n,b2}$ is a geometric mean value of $E_n$ and $E_{n-1}$, and $E_n$ and $E_{n-1}$ are amplification efficiencies at $n^{th}$, and $(n-1)^{th}$ cycles respectively, in which n is an integer greater than or equal to 3, $$\overline{E}_{n,b3}=[(1+E_{n-2})(1+E_{n-1})(1+E_n)]^{1/3}-1 \quad \text{(Formula 6)},$$

wherein $\overline{E}_{n,b3}$ is a geometric mean value of $E_{n-2}$, $E_{n-1}$ and $E_n$, and $E_{n-2}$, $E_{n-1}$ and $E_n$ are amplification efficiencies at $(n-2)^{th}$, $(n-1)^{th}$, and $n^{th}$ cycles respectively, in which n is an integer greater than or equal to 4, $$\overline{E}_{n,b4}=[(1+E_{n-3})(1+E_{n-2})(1+E_{n-1})(1+E_n)]^{1/4}-1 \quad \text{(Formula 7)}$$

wherein $\overline{E}_{n,b4}$ is a geometric mean value of $E_{n-3}$, $E_{n-2}$, $E_{n-1}$ and $E_n$, and $E_{n-3}$, $E_{n-2}$, $E_{n-1}$ and $E_n$ are amplification efficiencies at $(n-3)^{th}$, $(n-2)^{th}$, $(n-1)^{th}$, and $n^{th}$ cycles respectively, in which n is an integer greater than or equal to 5, and $$\overline{E}_{n,b5}=[(1+E_{n-4})(1+E_{n-3})(1+E_{n-2})(1+E_{n-1})(1+E_n)]^{1/5}-1 \quad \text{(Formula 8)},$$

wherein $\overline{E}_{n,b5}$ is a geometric mean value of $E_{n-4}$, $E_{n-3}$, $E_{n-2}$, $E_{n-1}$ and $E_n$, and $E_{n-4}$, $E_{n-3}$, $E_{n-2}$, $E_{n-1}$ and $E_n$ are amplification efficiencies at $(n-4)^{th}$, $(n-3)^{th}$, $(n-2)^{th}$, $(n-1)^{th}$, and $n^{th}$ cycles respectively, in which n is an integer greater than or equal to 6.

25. The method of claim 18, wherein the geometric mean value is represented by any one of Formulae 9 to 12 below:

$$\overline{E}_{n,f2}=[(1+E_n)(1+E_{n+1})]^{1/2}-1 \quad \text{(Formula 9)},$$

wherein $\overline{E}_{n,f2}$ is a geometric mean value of $E_n$ and $E_{n+1}$, and $E_n$ and $E_{n+1}$ are amplification efficiencies at $n^{th}$ and $(n+1)^{th}$ cycle respectively, in which n is an integer greater than or equal to 2, $$\overline{E}_{n,f3}=[(1+E_n)(1+E_{n+1})(1+E_{n+2})]^{1/3}-1 \quad \text{(Formula 10)},$$

wherein $\overline{E}_{n,f3}$ is a geometric mean value of $E_n$, $E_{n+1}$, and $E_{n+2}$, and $E_n$, $E_{n+1}$ and $E_{n+2}$ are amplification efficiencies at $n^{th}$, $(n+1)^{th}$, and $(n+2)^{th}$ cycle respectively, in which n is an integer greater than or equal to 2, $$\overline{E}_{n,f4}=[(1+E_n)(1+E_{n+1})(1+E_{n+2})(1+E_{n+3})]^{1/4}-1 \quad \text{(Formula 11)},$$

wherein $\overline{E}_{n,f4}$ is a geometric mean value of $E_n$, $E_{n+1}$, $E_{n+2}$ and $E_{n+3}$, and $E_n$, $E_{n+1}$, $E_{n+2}$ and $E_{n+3}$ are amplification efficiencies at $n^{th}$, $(n+1)^{th}$, $(n+2)^{th}$, and $(n+3)^{th}$ cycle respectively, in which n is an integer greater than or equal to 2, $$\overline{E}_{n,f5}=[(1+E_n)(1+E_{n+1})(1+E_{n+2})(1+E_{n+3})(1+E_{n+4})]^{1/5}-1 \quad \text{(Formula 12)},$$

wherein $\overline{E}_{n,f5}$ is a geometric mean value of $E_n$, $E_{n+1}$, $E_{n+2}$, $E_{n+3}$ and $E_{n+4}$, and $E_n$, $E_{n+1}$, $E_{n+2}$, $E_{n+3}$ and $E_{n+4}$ are amplification efficiencies at $n^{th}$, $(n+1)^{th}$, $(n+2)^{th}$, $(n+3)^{th}$, and $(n+4)^{th}$ cycle respectively, in which n is an integer greater than or equal to 2.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Forward primer
```

-continued

```
<400> SEQUENCE: 1
agtgtggatt cgcactcct                                              19

<210> SEQ ID NO 2
<211> LENGTH: 23
<212> TYPE: DNA
<213> ORGANISM: Artificial Sequence
<220> FEATURE:
<223> OTHER INFORMATION: Reverse primer

<400> SEQUENCE: 2
gagttcttct tctaggggac ctg                                         23
```